US009259598B2

(12) United States Patent     (10) Patent No.: US 9,259,598 B2
Stewart et al.     (45) Date of Patent: Feb. 16, 2016

(54) AQUEOUS DISPERSIONS OF CRYSTALLINE POLYMERS AND USES

(75) Inventors: Ray F. Stewart, Redwood City, CA (US); Natarajan Balachander, Sunnyvale, CA (US); Steven P. Bitler, Menlo Park, CA (US); Loc Phan, San Jose, CA (US); Valentine Y. Yoon, Santa Barbara, CA (US)

(73) Assignee: Landec, Inc., Menlo Park, CA (US)

( * ) Notice: Subject to any disclaimer, the term of this patent is extended or adjusted under 35 U.S.C. 154(b) by 2876 days.

(21) Appl. No.: 11/637,655

(22) Filed: Dec. 12, 2006

(65) Prior Publication Data

US 2007/0104745 A1     May 10, 2007

Related U.S. Application Data

(60) Division of application No. 10/321,187, filed on Dec. 17, 2002, now Pat. No. 7,175,832, which is a continuation of application No. 09/764,552, filed on Jan. 18, 2001, now Pat. No. 6,540,984, which is a continuation of application No. 09/210,421, filed on Dec. 11, 1998, now abandoned, which is a continuation-in-part of application No. 08/766,865, filed on Dec. 12, 1996, now abandoned, and a continuation-in-part of application No. 08/769,639, filed on Dec. 12, 1996, now abandoned, and a continuation-in-part of application No. 08/929,750, filed on Sep. 15, 1997, now Pat. No. 6,199,318.

(51) Int. Cl.

| | |
|---|---|
| *A61K 9/00* | (2006.01) |
| *A61K 9/50* | (2006.01) |
| *A61Q 5/06* | (2006.01) |
| *A01C 1/06* | (2006.01) |
| *A61K 8/02* | (2006.01) |
| *A61K 8/81* | (2006.01) |
| *A61Q 5/00* | (2006.01) |
| *B05D 7/00* | (2006.01) |
| *C09D 133/14* | (2006.01) |
| *D06M 15/263* | (2006.01) |

(52) U.S. Cl.

CPC ... *A61Q 5/06* (2013.01); *A01C 1/06* (2013.01); *A61K 8/0237* (2013.01); *A61K 8/8152* (2013.01); *A61K 8/8158* (2013.01); *A61Q 5/00* (2013.01); *B05D 7/00* (2013.01); *C09D 133/14* (2013.01); *D06M 15/263* (2013.01); *A61K 2800/54* (2013.01); *D06M 2200/20* (2013.01)

(58) Field of Classification Search

None
See application file for complete search history.

(56) References Cited

U.S. PATENT DOCUMENTS

| | | | |
|---|---|---|---|
| 3,598,565 A | 8/1971 | Graves | 71/77 |
| 3,644,241 A | 2/1972 | Falivens | 260/17.4 |
| 3,707,807 A | 1/1973 | Graves | 47/57.6 |
| 3,716,524 A | 2/1973 | Cenci | 260/78.5 |
| 3,833,393 A | 9/1974 | Kandathil | 106/212 |
| 3,992,485 A * | 11/1976 | Kosugi et al. | 525/261 |
| 4,104,824 A | 8/1978 | Lundberg | 47/58 |
| 4,184,020 A | 1/1980 | Coupek | 521/52 |
| 4,196,190 A | 4/1980 | Gehman | 424/47 |
| 4,251,952 A | 2/1981 | Porter | 47/57.6 |
| 4,272,417 A | 6/1981 | Berke | 260/22 R |
| 4,401,688 A | 8/1983 | Garnett | 427/43.1 |
| 4,439,495 A | 3/1984 | Tobias | 428/463 |
| 4,448,796 A | 5/1984 | Wieser | 427/4 |
| 4,452,261 A | 6/1984 | Bresek | 132/7 |
| 4,729,190 A | 3/1988 | Lee | 47/57.6 |
| 4,735,017 A | 4/1988 | Gage | 7/57.6 |
| 4,780,499 A | 10/1988 | Villareal | 524/549 |
| 4,791,184 A | 12/1988 | Nagai | 526/323.2 |
| 4,834,968 A | 5/1989 | Bolich | 424/47 |
| 4,925,908 A * | 5/1990 | Bernard et al. | 526/320 |
| 4,983,383 A | 1/1991 | Maksimoski | 424/70 |
| 5,009,880 A | 4/1991 | Grollier | 424/47 |
| 5,021,525 A | 6/1991 | Montague | 526/210 |
| 5,025,062 A | 6/1991 | Ley | 4/556 |
| 5,044,116 A | 9/1991 | Gage | 7/57.6 |
| 5,087,475 A | 2/1992 | Bazin | 427/4 |
| 5,100,944 A | 3/1992 | Walker | 524/306 |
| 5,104,642 A | 4/1992 | Wells | 424/47 |
| 5,106,648 A | 4/1992 | Williams | 427/3 |
| 5,127,185 A | 7/1992 | Kojimoto | 47/57.6 |
| 5,129,180 A | 7/1992 | Stewart | 47/57.6 |
| 5,194,469 A | 3/1993 | Srail | 524/166 |
| 5,225,480 A * | 7/1993 | Tseng et al. | 524/813 |
| 5,250,082 A | 10/1993 | Teng | 7/57.6 |
| 5,284,907 A | 2/1994 | Shulz | 524/710 |
| 5,300,127 A | 4/1994 | Williams | 47/57.6 |
| 5,314,530 A | 5/1994 | Wiener | 108/2 |
| 5,318,995 A | 6/1994 | Mondet | 514/772.1 |
| 5,324,762 A | 6/1994 | Overand | 524/296 |
| 5,369,163 A | 11/1994 | Chiou | 524/458 |

(Continued)

FOREIGN PATENT DOCUMENTS

| | | |
|---|---|---|
| JP | 6-192341 | 7/1994 |
| WO | WO 92-10081 | 6/1992 |

(Continued)

*Primary Examiner* — Robert A Wax
*Assistant Examiner* — William Craigo
(74) *Attorney, Agent, or Firm* — Tim Richardson; James McDonald (57) ABSTRACT

Aqueous dispersions of crystalline polymers based on hydrophobic monomers, preferably on a mixture of hydrophobic and hydrophilic monomers which contains a crosslinking monomer, particularly side chain crystalline (SCC) polymers. The dispersions are useful for providing coatings on substrates, particularly on seeds (whose dormancy is thus extended) and on fibrous substrates, particularly human hair (which thus becomes heat-settable).

19 Claims, 4 Drawing Sheets

(56) References Cited

U.S. PATENT DOCUMENTS

| | | | | |
|---|---|---|---|---|
| 5,387,450 A | * | 2/1995 | Stewart | 428/40.4 |
| 5,391,368 A | | 2/1995 | Gerstein | 424/17.13 |
| 5,478,553 A | | 12/1995 | Chandran | 424/70.1 |
| 5,516,865 A | * | 5/1996 | Urquiola | 526/329.7 |
| 5,632,977 A | | 5/1997 | Chandran | 424/70.17 |
| 5,736,125 A | | 4/1998 | Morawsky | 424/59 |

FOREIGN PATENT DOCUMENTS

| | | |
|---|---|---|
| WO | WO 93-21967 | 11/1993 |
| WO | WO 96-27641 | 9/1996 |

\* cited by examiner

AQUEOUS DISPERSIONS OF CRYSTALLINE POLYMERS AND USES

CROSS-REFERENCE TO RELATED APPLICATIONS

This application is a division of copending, commonly assigned application Ser. No. 10/321,187, filed Dec. 17, 2002, which is a continuation of application Ser. No. 09/764,552, filed Jan. 18, 2001, now U.S. Pat. No. 6,540,984, which is a continuation of application Ser. No. 09/210,421, filed Dec. 11, 1998, now abandoned. Application Ser. No. 09/210,421 is a continuation-in-part of application Ser. No. 08/766,865, filed Dec. 12, 1996, now abandoned; application Ser. No. 08/769,639, filed Dec. 12, 1996, now abandoned; and application Ser. No. 08/929,750, filed Sep. 15, 1997, now U.S. Pat. No. 6,199,318. This application also claims priority under 35 USC 365 (a) and 35 USC 119 from PCT Application No. PCT/US 97/22772, filed Dec. 12, 1997. The disclosure of each of those applications is incorporated herein by reference in their entireties.

BACKGROUND OF THE INVENTION

This invention relates to aqueous dispersions of crystalline polymers, methods for making such dispersions and the use of such dispersions for coating substrates.

It is known to use certain organic polymers to provide coatings on a wide variety of substrates, including hair (see U.S. Pat. Nos. 4,196,190; 4,452,216; 4,834,968 and 4,983,383); fabrics (see U.S. Pat. Nos. 3,644,241; 3,833,393 and 4,780,499); and seeds and other organisms (see U.S. Pat. No. 5,129,180). It is also known to set a fabric by impregnating the fabric with a monomer component, and polymerizing the monomer while maintaining the fabric in a desired configuration (see U.S. Pat. No. 4,401,688).

One class of polymers which has been used for coating substrates comprises side-chain crystalline ("SCC") polymers. However, the known coating compositions containing SCC polymers have the disadvantage that the polymer is dissolved in an organic solvent. Organic solvents are expensive, require environmental controls, and are particularly undesirable for application to human hair or to an organism.

Attempts have been made to prepare aqueous dispersions of SCC polymers (see *British Polymer Journal* 20, 521-524 (1988), U.S. Pat. Nos. 5,506,307 and 5,516,865, and Japanese Patent Document No. 6-192341), but the results have been poor and/or the techniques expensive.

SUMMARY OF THE INVENTION

We have discovered, in accordance with the present invention, that very valuable results can be achieved by coating substrates with aqueous dispersions of polymeric particles in which the polymer is a crystalline polymer containing units derived from at least one hydrophobic monomer and preferably also from a lesser amount of units derived from at least one hydrophilic monomer. Particularly useful results are obtained when the substrate is a seed or other organism, or a fibrous material. We have also discovered, in accordance with the invention, novel aqueous dispersions of crystalline polymers and methods of making such dispersions.

In one of its embodiments, this invention provides a substrate having a solid polymeric coating thereon, the coating having been obtained by:
(1) applying to the substrate an aqueous dispersion of solid particles comprising a crystalline polymer, the polymer
  (a) having a melting point $T_m$ and (b) comprising units derived from a hydrophobic monomer, and
(2) evaporating water from the dispersion to form the solid polymeric coating;
the coating having at least one of the following characteristics:
(A) at temperatures below $T_m$, the coating is substantially impermeable to water (as hereinafter defined), and at temperatures above $T_m$, the coating is substantially permeable to water (as hereinafter defined);
(B) the polymer is a crosslinked polymer having a gel content of at least 50%,
(C) the polymer is derived from a monomer component comprising:
  (i) a hydrophobic monomer component comprising a first hydrophobic monomer, the first hydrophobic monomer being such that a homopolymer thereof is crystalline and has a melting point $T_c$, and
  (ii) a hydrophilic monomer component comprising a hydrophilic monomer, the ratio by weight of the hydrophobic monomer component to the hydrophilic monomer component being 10:1 to 50:1;
(D) the polymer is derived from a monomer component comprising a hydrophobic monomer component comprising (i) a first hydrophobic monomer, the first hydrophobic monomer being such that a homopolymer thereof is crystalline and has a melting point $T_c$, and (ii) a second hydrophobic monomer which
  (a) is such that a homopolymer thereof is amorphous and has a glass transition point $T_g$ which is less than $T_c$, and
  (b) is present in amount such that $T_m$ is $(T_c-5)°$ C. or less;
(E) the polymer is derived from a monomer component comprising a hydrophobic monomer component comprising (i) a first hydrophobic monomer, the first hydrophobic monomer being such that a homopolymer thereof is crystalline and has a melting point $T_c$, and (iii) a second hydrophobic monomer which
  (a) is such that a homopolymer thereof is amorphous and has a glass transition point $T_g$ which is more than $T_c$, and
  (b) is present in amount such that the coating has a tack at $(T_c+10)°$ C. which is less than the tack at $(T_c+10)°$ C. of a coating formed under the same conditions from a composition which is identical except that the crystalline polymer does not contain units derived from the second hydrophobic monomer;
(F) the polymer is derived from a monomer component comprising:
  (i) a hydrophobic monomer component comprising a hydrophobic monomer, the hydrophobic monomer being such that a homopolymer thereof is crystalline and has a melting point $T_c$;
  (ii) a hydrophilic monomer component comprising a hydrophilic monomer; and
  (iii) a crosslinking monomer having at least two polymerizable groups;
(G) the polymer is derived from a monomer component comprising one or more monomers containing carboxyl groups, at least 75% of the carboxyl groups having been neutralized;
(H) the polymer is crosslinked by an external crosslinker (as hereinafter defined);
(I) the particles of the dispersion have coalesced to form a continuous coating, but retain a particulate character;
(J) the coating contains less than 1% of unreacted monomer, based on the weight of the polymer; and (K) at least some of the particles comprise a core comprising said crystalline polymer and a coating around the core comprising a substantially amorphous polymer.

In describing the invention below, unless otherwise noted, parts, percentages and ratios are by weight. The monomers from which the crystalline polymer is derived are important. The term hydrophobic monomer is used herein to denote a monomer whose solubility in water at 25° C. is less than 2%. The term hydrophilic monomer is used herein to denote a monomer whose solubility in water at 25° C. is 2% or more. More than one hydrophobic monomer can be used, and the term hydrophobic monomer component is used herein to denote all the hydrophobic monomers collectively, and is often abbreviated herein to "BMC." More than one hydrophilic monomer component can be used, and the term hydrophilic monomer component is used herein to denote all the hydrophilic monomers collectively, and is often abbreviated herein to "PMC." The monomers from which the crystalline polymer is derived can include one or more monomers which contain two or more polymerizable groups, so that the polymer is crosslinked. Such monomers (which may be hydrophobic or hydrophilic) are referred to herein as crosslinking monomers; and the term crosslinking monomer component is used herein to denote all the crosslinking monomers collectively, and is often abbreviated herein to "XLC." Except where otherwise noted, percentages of monomers given herein (both as starting materials, and as residual monomers) are based on the total weight of the monomer starting material. As further discussed below, the monomers used in preparing the crystalline polymers are preferably n-alkyl acrylates or methacrylates. The abbreviation CnA and 'CnMA are used to denote n-alkyl acrylates and n-alkyl methacrylates, respectively, in which the n-alkyl group contains x carbon atoms. For example C4A denotes butyl acrylate, and C12MA denotes lauryl methacrylate.

Crystalline melting points given herein ($T_m$ and $T_c$) are the peak of a curve produced using a differential scanning calorimeter (DSC) as a heating rate of 10° C. per minute, and using the second heat cycle. The onset of melting ($T_o$) is taken from the same curve. $T_o$, $T_m$ and $T_c$ are measured in the conventional way well known to those skilled in the art. Thus, $T_m$ and $T_c$ are the temperature at the peak of the DSC curve and $T_o$ is the temperature at the intersection of the baseline of the DSC peak and the onset line, the onset line being defined as the tangent to the steepest part of the DSC curve below the peak. Tack values given herein are measured as follows. The latex is applied to a polymeric film (a polyester film available from DuPont under the trade name "Mylar," or a filled polyethylene film available from PPG under the trade name "Teslin"), at a rate such that after the coating has been dried at 65° C. for 2 hours, it has a thickness of about 30 microns. Two such films are laminated together at 35° C. and the tack is measured with a vslip/peel tester at 230 cm/min.

In a first preferred aspect, this invention provides a method of treating an organism to extend its dormancy, the method comprising (1) applying to the organism a non-phytotoxic coating composition which comprises (a) water, and (b) suspended in the water, particles which comprise a crystalline polymer having a melting point $T_m$ of 0° to 40° C.; and (2) causing water to evaporate from the composition, thereby forming on the organism a coating which (a) at temperatures below $T_m$ is substantially impermeable to water and (b) at temperatures above $T_m$ is substantially permeable to water.

In a second preferred aspect, this invention provides a composition which comprises:
(a) water,
(b) suspended in the water, particles comprising a crosslinked crystalline polymer which
(i) has a gel content of at least 50%,
(ii) contains less than 1% of unreacted monomer, and
(iii) is derived from a monomer component comprising:
1) a hydrophobic monomer component comprising a first hydrophobic monomer, the first hydrophobic monomer being such that a homopolymer thereof is crystalline and has a melting point $T_c$, and
2) a hydrophilic monomer component comprising a hydrophilic monomer, and
3) a crosslinking monomer having at least two polymerizable groups; and
(c) a surfactant.

In a third preferred aspect, this invention provides a method of making a composition in accordance with the second preferred aspect, the method comprising:
(a) providing an aqueous reaction medium comprising:
(i) water,
(ii) the monomer component, the monomer component containing at least 2% of the hydrophilic monomer component,
(iii) the surfactant, and
(iv) at least 1% based on the water, of a cosolvent which increases the solubility of the hydrophobic monomer component in the water;
(b) polymerizing the monomer component in the aqueous reaction medium so that at least 99% thereof polymerizes to form the crystalline polymer in the form of particles having an average particle size less than 0.5 microns, the monomer component being present in amount such that at the end of the polymerization, the solid polymer content of the reaction mixture is at least 30%; and
(i) the surfactant being present in amount such that the monomer component is initially present in the aqueous reaction medium in the form of droplets having a diameter greater than 10 microns, and/or
(ii) the surfactant and the cosolvent being present in amount such that the hydrophilic monomer component is substantially randomly polymerized in the crystalline copolymer.

In a fourth preferred aspect, this invention provides a method for preparing an aqueous suspension, the method comprising the steps of:
(a) providing an aqueous reaction medium comprising:
(i) water,
(ii) a first monomer component comprising a hydrophobic monomer component comprising a first hydrophobic monomer, the first hydrophobic monomer being such that a homopolymer thereof is crystalline, and
(iii) a surfactant;
b) polymerizing the first monomer component to form a crystalline polymer in the form of particles suspended in the reaction mixture; and
c) polymerizing a second monomer component to form a shell on said particles,
the amounts of said first and second monomer components being such that the product of step (c) has a solids content of at least 30%, and
the amount of surfactant being such that the product of step (c) contains particles having an average particle size of less than 0.5 microns and a residual monomer content of less than 1%.

In a fifth preferred aspect, this invention provides a composition suitable for use in setting a fibrous material, the composition comprising:
  (a) water;
  (b) particles suspended in the water, the particles comprising a crystalline polymer; and
  c) an effective amount of an additive having a desired effect on the fibrous material. The term "effective amount" is used herein to denote an amount which is sufficient to provide the fibrous material with desired benefits, taking into consideration the thickness, density, length and texture of the fibers.

In a sixth preferred aspect, this invention provides a method of coating a fibrous material, the method comprising:
  (1) applying to the fibrous material a composition in accordance with the fifth aspect of the invention; and
  (2) evaporating the water from the composition while the composition is in contact with the fibrous material, thereby forming a coating on the fibrous material.

This method can further comprise:
  (3) while the coating is at a temperature above $T_m$, setting the fibrous material into a first desired configuration; and
  (4) cooling the coating to below $T_m$ while maintaining the fibrous material in the first desired configuration.

If desired, the method can further comprise:
  (5) reheating the coating to a temperature greater than $T_m$;
  (6) after reheating the coating, and while the coating is at a temperature above $T_m$, setting the fibrous material into a second desired configuration which is the same as or different from the first desired configuration; and
  (7) cooling the coating while maintaining the fibrous material in the second desired configuration.

The term "cooling the coating" includes merely leaving the coated material to cool in the ambient atmosphere, as well as methods in which active steps are taken to effect cooling. Fibrous materials which can be used include hair, particularly human hair, and woven, knitted and non-woven fabrics and other textile products such as grains, including cotton and cotton/polyester blend materials.

It is to be understood that in the foregoing description of the invention, and in the more detailed description set forth below, the various features which are disclosed may be used in any appropriate combination, and features which are disclosed in connection with a particular embodiment can be used singly or in combination in connection with the invention in general and in connection with other embodiments, except of course where the features are mutually exclusive.

DETAILED DESCRIPTION OF THE INVENTION

A. Materials for Use in the Preparation of the Polymeric Dispersions

In order to prepare the aqueous polymeric dispersions which form part of the present invention, and/or which can be used to coat substrates in accordance with the invention, a monomer component is dispersed in water with the aid of a surfactant and preferably a cosolvent; optionally other additives may also be present. The reaction mixture is then subjected to conditions which cause the monomer(s) to react to form a polymer which remains in suspension in the reaction medium. The monomer component comprises a hydrophobic monomer component (BMC) and preferably also a hydrophilic monomer component (LMC). Either the BMC or the LMC, or both, can include a crosslinking monomer. The reaction mixture can also contain a crosslinking agent, which can be (a) a crosslinking monomer component (XLC) which comprises at least one monomer containing at least two polymerizable groups, or (b) an "external crosslinker." An external crosslinker is a compound which increases the apparent molecular weight of the polymer without becoming a covalently bound part of the polymer, and which increases the mechanical strength of coatings formed from the aqueous dispersion of the polymer.

1. Monomer Components (a) Hydrophobic Monomer Component (BMC)

The BMC comprises at least one first hydrophobic monomer such that a homopolymer thereof is crystalline and has a melting point $T_c$. It may also be desirable for the BMC to include at least one second hydrophobic monomer such that a homopolymer thereof is amorphous and has a glass transition point $T_g$. In one embodiment, $T_g$ is less than $T_c$ and the second hydrophobic monomer is present in amount such that the $T_m$ of the polymer is $(T_c-5)°$ C. or less. In another embodiment, $T_g$ is more than $T_c$, in which case the amount of the second hydrophobic monomer is preferably such that a coating formed from the composition has a tack at $(T_c+10)°$ C. which is less than the tack at $(T_c+10)°$ C. of a coating formed under the same conditions from a composition which is identical except that the crystalline polymer does not contain units derived from the second hydrophobic monomer. The amount of the second hydrophobic monomer is generally less than 50%, preferably 5 to 40%, particularly 5 to 30%, based on the BMC.

Preferred hydrophobic monomers are $\propto$, β-ethylenically-unsaturated monomers, particularly n-alkyl acrylates and n-alkyl methacrylates in which the n-alkyl groups contains 4 to 24 carbons.

Preferred first hydrophobic monomers are monomers whose homopolymers are side chain crystalline (SCC) polymers. SCC polymers are well known, and are described for example in the following publications, to which reference should be made for a more complete disclosure of first hydrophobic monomers suitable for use in this invention: J. Poly. Sci. 60, 19 (1962), J. Poly. Sci. (Polymer Chemistry) 7, 3053 (1969), 9, 1835, 3349, 3351, 3367, 10, 1657, 3347, 18, 2197, 19, 1871, J. Poly. Sci., Poly Physics Ed 18 2197 (1980), J. Poly. Sci. Macromol. Rev. 8, 117 (1974), Macromolecules 12, 94 (1979), 13, 12, 15, 18, 2141, 19, 611, JACS 75, 3326 (1953), 76, 6280, Polymer J 17, 991 (1985), Poly. Sci USSR 21, 241 (1979), U.S. Pat. Nos. 4,380,855, 5,120,349, 5,129, 180, 5,156,411, 5,254,354, 5,387,450, 5,412,035, 5,469,869, and 5,665,822. Particularly preferred first hydrophobic monomers are those which result in SCC polymers in which the side chain comprises a linear polymethylene group containing 12 to 50, preferably 14 to 22, carbons, or a linear perfluorinated or substantially perfluorinated polymethylene group containing 6 to 50 carbons. Mixtures of such hydrophobic monomers can be used. Preferred monomers are those which are commercially available, in particular the n-alkyl acrylates. Preferred first hydrophobic monomers for use in the invention comprise at least one of C12MA, C12A, C14A, C14MA, C16A, C16M, C18A, mixtures of C18A, C20A and C22A, mixtures of C26A and C40A, fluorinated C8A, and mixtures of fluorinated C8A, C10A and C12A, and other monomers which produce substantially the same final polymers, e.g. acrylamides and methacrylamides.

Preferred second hydrophobic monomers are monomers whose homopolymers have a $T_g$ of −50 to 120° C., for example n-butyl and t-butyl acrylate, homopolymers of which have melting points off 32, 65, 107, 28, 10, 40, and 52° C., respectively. Examples of suitable second hydrophobic monomers of linear and branched chain alkyl, hydroxyalkyl and alkoxy alkyl acrylates, methacrylates, acrylamides, and methacrylamides, and vinyl esters, in particular C8A, C8MA, 2-ethylhexyl acrylate and methacrylate, C6A, C6MA, C4A, C4MA and mixtures thereof.

(b) Hydrophilic Monomer Component (LMC)

The LMC comprises at least one hydrophilic monomer and is preferably present in an amount of 2 to 10%, particularly 2 to 5%. The hydrophilic monomer is preferably an $\alpha\beta$-ethylenically unsaturated monomer, for example a vinylic compound such as acrylic acid; methacrylic acid; an alkyl, hydroxyalkyl or alkoxyalkyl acrylate or methacrylate (e.g. hydroxy ethyl methacrylate); acrylamide and methacrylamide; acrylic or methacrylic acid; acrylamide; methacrylamide; maleic anhydride; itaconic acid; a comonomer containing an amine group: and 2-acrylamido-2-methylpropane sulfonic acid (AMPS) and combinations thereof. Preferably the hydrophilic monomer is selected from the group consisting of acrylic acid, methacrylic acid, itaconic acid, 2-acrylamido-2-methylpropane sulfonic acid, acrylamide, methacrylamide, or hydroxyethyl (meth)acrylate or a mixture thereof.

(c) Crosslinking Monomer Component (XMC)

The XMC, if present, comprises at least one crosslinking monomer which contains at least two polymerizable groups, e.g. vinylic groups. The XMC is preferably used in amount such that the polymer has a gel content of at least 50%, particularly at least 60%, up to substantially 100%. Preferred hydrophobic crosslinking monomers include 1,4-butanediol diacrylate, 1,6-hexanediol diacrylate, 1,14-tetradecyldiol diacrylate, divinyl benzene, vinyl crotonate, divinyl ether, and 1,3,5-triallyl triazine trione, and mixtures thereof. Preferred hydrophilic crosslinking monomers include ethylene glycol diacrylate, and ethylene glycol dimethacrylate, and mixtures thereof.

The amount of crosslinking monomer is preferably such that the polymer has a crosslink density (number of crosslinks per weight average molecular weight) of at least 0.01, preferably at least 0.05, particularly at least 0.1, so that the polymer resists flow above $T_m$. A high gel content (e.g. crosslinking beyond 1 to 10 mole percent) is not generally needed and can result in decreased crystallinity and poor performance. The crosslinked polymer preferably has a heat of fusion of at least 10, preferably at-least 20, J/g.

The use of an XMC is important when it is desirable for the coating to be easily removed, because the resulting crosslinked particles are harder; and when water is evaporated from the dispersion, the particles do not easily diffuse into each other. The resulting coatings have a particulate character and as a result are more easily removable and frangible. This is particularly important for hair-setting compositions, since it is desirable that the film-forming material be removable by washing hair with water. It is also particularly important for seed coatings; prior art non-particulate coatings can remain on the seed and inhibit seed germination. In the absence of cross-linking, when the water is evaporated, the latex particles are brought together by capillary action, and water is squeezed out from the interstitial spaces. The particles coalesce and lose their identity, and a substantially uniform film results.

(d) Carboxyl-Containing Monomer Component

The monomer component can contain one or more monomers containing carboxyl groups, the carboxyl groups being partially, preferably at least 75%, neutralized (e.g. with NaHCO$_3$) after the polymerization is complete.

(e) Preferred Monomer Components

Preferred monomer components result in a crystalline polymer having a sharp melting point, preferably such that ($T_m$-$T_o$) is less than 20° C., preferably less than 15° C., particularly less than 10° C., where $T_o$ is the onset of melting on the DSC curve.

Particularly preferred monomer components comprise:
(i) 50 to 100%, preferably 65 to 95%, of at least one first hydrophobic monomer which is an alkyl acrylate, alkyl methacrylate, alkyl acrylamide, alkyl methacrylamide, alkyl vinyl ether or alkyl vinyl ester in which the alkyl group is an n-alkyl group containing 12 to 50 carbon atoms:
(ii) 0 to 35% of at least one second hydrophobic monomer which is an alkyl acrylate, alkyl methacrylate, N-alkyl acrylamide, alkyl vinyl ether, or alkyl vinyl ester in which the alkyl group is an n-alkyl group containing 4 to 12 carbon atoms; and
(iii) at least 2%, and preferably no more than 10% of at least one hydrophilic monomer which is acrylic acid, methacrylic acid, 2-acrylamido-2-methylpropane sulfonic acid, hydroxyethyl acrylate or methacrylate itaconic acid, acrylamide, methacrylamide, acrylonitrile, methacrylonitrile, a tetraalkylammonium acrylate, vinyl acetate or N-vinyl pyrrolidone.

2. External Crosslinkers

External crosslinkers, when used, are generally compounds containing charged groups which interact with charged groups in the polymer. Preferred external crosslinkers contain metal (e.g. Mg, Mn, Zn, Ca, Ti or Zr) cations or bidentate or multidentate amine groups. Other external crosslinkers are non-metallic and organic compounds, e.g. triethylene tetramine, ethylene diamine, diethyl aminopropylamine and bis(quaternary ammonium) salts. The amount of external crosslinker is generally 0.1 to 10, preferably 0.5 to 3%, based on the monomer component. Some external crosslinkers do not have any effect until a coating is prepared from the dispersion. For example, the cation can be present as an ammonia complex and not become effective until the ammonia is removed during the evaporation step. Thus, an aqueous solution containing $Zn(NH_3)^{++}$ ions can be used in this way.

External crosslinkers can be used in combination with crosslinking monomers.

3. Surfactants

The reaction medium for the polymerization comprises at least one surfactant, preferably at least one ionic surfactant and at least one non-ionic surfactant, to suspend and stabilize the particles formed by polymerizing the monomer component in the aqueous reaction medium. The amount of surfactant can be 0.8 to 10%, preferably 1 to 5%, based on the reaction medium. However, the optimum amount of surfactant depends also on the amount of cosolvent present, as further described below. Preferably, sufficient surfactant is present to enable the monomer component to be present initially as droplets having a diameter of more than 10 microns.

Surfactants are characterized by a hydrophile-lipophile balance (HLB) number that describes the strength of the hydrophilicity to the lipophilicity of the surfactant. Anionic surfactants having a HLB number of 20 to 40 are preferably used, and function to form micelles at low concentrations and to act as nucleation sites for the latex particles. Once nucleation is complete, the surfactants can additionally provide charge stabilization to the growing latex particles. Preferably the anionic surfactants contain a sulfate or sulfonate group and a hydrophobic moiety and may be, for example, alkyl sulfates, alkyl ether sulfonates and sulfates, alkylaryl sulfonates, and sulfosuccinates. Preferred anionic surfactants are the amine salt of dodecyl benzene sulfonic acid, salts of dioctyl sulfosuccinate, salts of lauryl sulfate, and salts of the ethoxylated alcohol half ester of sulfosuccinic acid. Exemplary alkyl and alkene sulfonates are described in U.S. Pat. Nos. 4,983,383 and 5,194,469.

Nonionic surfactants having HLB numbers of 5 to 35, e.g. 5 to 30, preferably 10 to 15, can also be employed. These surfactants lower the interfacial tension between the monomer oil droplets and the aqueous phase, and provide stabilization of the polymer dispersion by partitioning at the interface of the aqueous phase and the polymer particles. Thus they reduce the polymer dispersion's sensitivity to shear, temperature and the presence of electrolytes. The nonionic surfactants can be linear or branched ethoxylated alcohols, ethoxylated alkylphenols, or block copolymers of ethylene oxide and propylene oxide. Preferably they contain 3 to 40 ethylene oxide repeat units and a hydrophobic moiety which may be a linear or branched $C_{11}$-$C_{15}$ secondary alcohol, nonylphenol or octylphenol, or are block copolymers of ethylene oxide and propylene oxide.

The amount of surfactant present is preferably such that high energy homogenization of the monomer component is not needed to form the latex. When little or no cosolvent is used, preferably a relatively large amount of surfactant (e.g. at least 5% based on the monomer component) is used so that the monomer component is dispersed in the reaction mixture as droplets having a diameter greater than 10 microns.

The amount of surfactant and cosolvent in the reaction mixture is preferably such that the units derived from the second hydrophobic monomer (if present) and/or the hydrophilic monomer are substantially randomly dispersed in the polymer.

The surfactant can be a polymerizable component which is incorporated into the polymer.

The choice of the surfactant may be influenced by the end use of the dispersion. For example, particularly useful surfactants for compositions used for coating corn seeds are fluorine-containing surfactants.

4. Cosolvents

The reaction medium preferably contains at least one cosolvent (also referred to as a diffusion modifier) which increases the solubility of the hydrophobic monomer in the reaction medium. It is generally present in amount at least 10% but less than 30%, preferably 5 to 20%, based on the water. Because the cosolvent increases the water solubility of the hydrophobic monomer, it increases the transport rate of the hydrophobic monomer from the monomer micelles or oil droplets to polymer nucleation sites. The cosolvents are preferably linear or branched monoalkanols containing 1 to 4 carbons, alkyl esters or alkyl ethers containing 1 to 6 carbons. Preferred cosolvents have a solubility in water of more than 0.7% at 25° C. and have boiling points of 60° to 130° C., preferably less than 95° C., so that they can be easily removed after the polymerization reaction. Preferred cosolvents include ethanol, isopropanol, ethyl acetate, n-propanol, sec-butanol, and t-butanol, and combinations thereof. Preferably the cosolvent has a water-octanol partition coefficient of at least 0.2 to enhance the solubility of the hydrophobic monomers in the water (see "Handbook of Property Estimation Methods," edited by W. J. Lyman, W. F. Reehl, D. H. Rosenblatt, American Chemical Society, Washington, D. C. 1990).

The amount of cosolvent preferably used depends upon the amount and type of surfactant used. For example, where there is about 1.6% of ionic and non-ionic surfactants, at least 5% of the cosolvent is generally required to obtain a single sharp melting point crystalline polymer, whereas when about 0.8% of ionic and non-ionic surfactants is present, at least about 10% of the cosolvent is generally required.

5. Initiators

A free radical initiator must generally be present to cause the polymerization to take place, generally in amount 0.1 to 0.4% based on the reaction mixture. Alternatively or additionally, ultraviolet radiation can be used to initiate the reaction.

Initiators useful in emulsion polymerization are well known [see, for example, U.S. Pat. No. 5,516,865 and "Emulsion Polymerization," Blackley (1975), chapter 6, Applied Science Publishers, London]. Suitable hydrophobic initiators for this invention include benzoyl peroxide and di-t-butyl peroxide. Suitable hydrophilic initiators include hydrogen peroxide and potassium and ammonium persulfate. A redox initiator, e.g. t-butyl hydroperoxide/ascorbic acid, or hydrogen peroxide/ferrous compound, can also be used.

6. Other Additives

The reaction mixture can contain a variety of other additives, including pH adjusters (e.g. sodium hydroxide and ammonium hydroxide); pH buffers (e.g. sodium bicarbonate and sodium hydrogen phosphate); coalescing agents (e.g. N-methylpyrrolidone, poly(ethylene glycol) alkyl ethers and poly(ethylene glycol); colloidal stabilizers (e.g. hydroxyethyl cellulose, polyacrylates and polyvinyl alcohols); rheology modifiers e.g. hydroxyethyl cellulose and the products available under the trade names Keizan and VCAR from Kelco and Union Carbide, respectively); and defoamers (e.g. the products available under the trade names Surfynol and Anti-foam H-10 Emulsion from Air Products and Dow Corning, respectively. The addition of sodium bicarbonate tends to increase particle size.

B. Polymerization Conditions

1. Single Stage Polymerization

The polymerization is generally carried out at 45 to 90° C., preferably 60 to 80° C. Lower temperatures decrease the amount of coagulum and increase particle size uniformity. Preferably the reaction is carried out under oxygen-free conditions, e.g. under nitrogen. Polymerization is preferably continued until at least 99% of the monomer component has been polymerized. Typically this takes 1 to 4 hours at about 70° C.

The polymerization is preferably carried out under conditions such that the polymer is obtained in the form of particles having an average size of less than 1 micron, preferably less than 0.5 micron, particularly 0.25 to 0.35 micron (measured by the well known light scattering technique). Small particle sizes are desirable because the dispersions are more stable, and do not clog spray nozzles. Preferably the amount of monomer is such that the reaction product has a solids content of at least 25%, particularly at least 30%, especially at least 35%. Higher solids content is desirable because less water needs to be evaporated to form a coating, and because the product is less expensive to package and transport. However, the solids content is generally no more than 45%, because of the tendency of very high solids content dispersions to coagulate spontaneously.

After the polymerization is complete, the cosolvent, if used, is generally removed. At this stage, further additives can be added to the latex, depending on the intended use of the product.

2. Two Stage Polymerization

In some applications it can be desirable in a first stage to polymerize the hydrophobic component thereby forming a crystalline copolymer or homopolymer, and then polymerizing the hydrophilic component in a second stage. This results in phase-separated particles having a core of predominantly (at least 50% by weight) crystalline polymer and a shell around the core, the shell being formed predominantly of non-crystalline polymer. Generally, the core is substantially all crystalline polymer as a first phase, and the shell is substantially all non-crystalline polymer as the shell. This is desirable when there is a need to change the properties of the crystalline polymer, such as tack, without changing the $T_m$. The monomers used to form the shell are not limited to hydrophilic materials, but can also be monomers such as styrene or butyl methacrylate.

For a core/shell product, $T_m$ is substantially the same as the crystalline homopolymer formed from the first hydrophobic monomer.

As in the single stage polymerization, the final latex preferably has a solids content of at least 30% and a residual monomer content of less than 1%; and the surfactant likewise preferably is present in amount such that the latex particles have an average particle size of less than 0.1 micron, particularly less than 0.5 micron.

C. Use of the Dispersions

The dispersions can be used to provide coatings on any solid substrate, e.g. fibers, seeds, or a shaped object. They can be applied to the substrate by means of conventional coating techniques such as wire-wound rod, direct gravure, offset gravure, reverse roll, air-knife, trailing blade coating, and spray coating. The coating is typically dried at a temperature at-least 5° C. above $T_m$ of the crystalline polymer, under ambient conditions or by the application of heat.

1. Coating of Fibrous Materials

Compositions for treating fibrous materials preferably (a) contain 2 to 50% by weight of the particles comprising the crystalline polymer, and/or (b) contain substantially no organic solvents, and/or (c) contain less than 1% by weight of residual monomer. Preferably the composition is a latex prepared as described above, and for many purposes the polymer has a $T_m$ of 20° to 60° C., particularly 40° to 60° C.

The composition can, for example, be dispensed from a pressurized container, or from a pump spray, or applied by means of a pad. The compositions can be used in place of starch, in which case the crystalline polymer has a $T_m$ usually from 40 to 60° C., which enables the polymer to be reset with an iron, but does not result in the polymer becoming reset in a clothes dryer. Alternatively, the polymer can give the fabric a "permanent press" character, by choosing a polymer having a $T_m$ sufficiently high that it does not easily reset, e.g. at least 60° C., preferably at least 80° C. A similar result can be achieved by crosslinking the crystalline polymer after the fabric has been coated, e.g. by using an external crosslinker.

Compositions for treating fabrics preferably include an effective amount of at least one fabric-treating additive, this term being used to denote any compound conventionally used to affect the properties of a fabric. The amount of each such additive is preferably at least 0.1% by weight of the composition. Suitable additives include perfumes, scents, stain resisters, optical brighteners, wetting agents, preservatives, softeners, ironing aids (typically 0.05 to 1.5% by weight of a silicone, e.g. dimethyl or methylphenyl silicone or an amine-modified silicone), anti-static agents, and bleaching agents (e.g. as described in Kirk-Othmer, *Encyclopedia of Chemical Technology,* 4th edition, John Wiley & Sons, volume 4, pages 271 et seq., and 552 et seq.). The composition can also contain a stabilizer, e.g. a naturally-occurring starch derived from corn, rice, wheat, or tapioca, or a modified starch, or carboxymethyl cellulose or a clay can also be employed.

Compositions for treating hair (particularly human hair, but also hair on a wig, or hair on a doll) preferably include an effective amount of at least one hair care additive, this term being used to denote any compound conventionally used in hair treating formulations. The amount of each such additive is preferably 0.01 to 10%, preferably 0.05 to 5%, based on the composition. Suitable additives include sequestering agents, hair-conditioning agents (e.g. cetyl trimethyl ammonium chloride, glyceryl monostearate, glycerin, propylene, glycol, sorbitol, urea, isopropyl myristate, balsam, lanolin, spermaceti, and isopropyl palmitate), anti-dandruff agents (e.g. sulfur, salicylic acid, resorcinol, bithionol, chloral hydrate, and zinc pyrithonel, reducing agents (e.g. thioglycolates), bleaching agents (e.g. hydrogen peroxide, and perborate and persulfate salts), scents, perfumes, pearlescent aids (e.g. ethylene glycol distearate), preservatives (e.g. benzyl alcohol, methylparaben, propylparaben, imidazolidinyl urea, and esters of p-hydroxybenzoic acid), thickeners (also known as viscosity modifiers, e.g. methyl cellulose, starches and starch derivatives), coloring agents (e.g. any of the FD&C or D&C dyes), and pH adjusting agents (e.g. citric acid, sodium citrate, succinic acid, phosphoric acid, sodium hydroxide, and sodium carbonate). Other hair care additives are described in the "COSMETIC INGREDIENT DICTIONARY" published by "THE COSMETIC TOILETRY AND FRAGRANCE ASSOCIATION INC.", U.S. Pat. No. 5,009,880, and Kirk-Othmer, *Encyclopedia of Chemical Technology,* 4th Ed., Vol. 12, John Wiley & Sons, pages 881-917.

The pH of the hair-treating composition is typically 3 to 9, preferably from 6 to 7. For application to human hair on a person, $T_m$ is preferably at least 40° C. so that the hair does not become unset at high ambient temperatures, but generally is no more than 60° C., so the hair can be reset with a hair dryer or curling iron. A particular advantage of the present invention is that the coatings can be applied to hair, and the hair can be repeatedly reset. Thus, the hair can be set in a desired configuration, and then by heating the crystalline polymer to a temperature greater than $T_m$, the hair can be reset into a second desired configuration. However, when the hair is on a wig or a doll, it can be desirable to set the hair more permanently. In such a case, $T_m$ is sufficiently high, preferably at least 60° C. Alternatively, or in addition, the composition can be externally crosslinked, as described above.

When a coating is formed on human hair, it is generally desirable that the coating can be easily removed by washing with water. This can be achieved by using a monomer component which contains (a) an XLC as described above, and/or (b) at least 0.5% of at least one amphoteric monomer, and/or (c) a carboxyl-containing monomer component as described above.

2. Coating of Seeds or Other Organisms

When seeds or other organisms are coated, the aqueous dispersion should be non-phytotoxic to the organism being coated. The dispersion is preferably applied by spray coating, the water then being evaporated by external heating or under ambient conditions. Other known application methods can be used. The thickness of the coating and the $T_m$ of the polymer are preferably such that the coating is substantially impermeable to water at temperatures below $T_m$. Generally, the $T_m$ of the polymer is from 0 to 40° C., preferably 10 to 35° C., and is equal to or greater than the lowest temperature at which the seed can germinate satisfactorily, and less than the highest temperature at which the seed can germinate satisfactorily. Preferably $T_m$ is substantially equal to, or greater than, the optimum germination temperature of the seed. Minimum, optimum and maximum germination temperatures for different seeds are known to, or can be determined by, those skilled in the art (see, for example, *Plant Propagation: Principles and Practice*, by Hartman and Kester, 1959). At temperatures above $T_m$, the coating becomes substantially permeable to water. In this way, the coating prevents substantial imbibition of water by the seed at too low a temperature, thus preventing "imbibitional chilling injury" and extending the dormancy of the seed, but permits the seed to imbibe water at temperatures at which germination can take place satisfactorily. It is not necessary for the coating to be completely impermeable to water at temperatures below $T_m$, and the term "substantially impermeable" should be understood accordingly. For example, the coating preferably ensures that the seed imbibes no more than 21%, more preferably no more than 17%, particularly no more than 15%, especially no more than 10%, of water over a period of 48 hours at temperatures below $T_m$. Similarly, the coating need not be completely permeable to water above $T_m$ and the term "substantially permeable" should be understood accordingly. For example, the coating preferably has a permeability to water above $T_m$ which is at least 2 times, particularly at least 3 times, its permeability below $T_m$. For example, at temperatures above $T_m$, the coating preferably permits the seed to imbibe. 25% or more, particularly 60% or more of water over a period of 48 hours at temperatures above $T_m$.

The permeability of the coating, as well as the value of $T_m$, can be adjusted for the needs of the particular seed. For example, for corn seed, the coating preferably prevents the seed from imbibing more than 10% of water over a period of 48 hours below $T_m$, but permits the seed to imbibe more than 10% of water over a period of 48 hours above $T_m$. More than one coating can be applied to the seed.

The polymers used for coating seeds are preferably derived from a monomer component which includes a second hydrophobic monomer. Polymers which lack such a monomer tend to be difficult to apply, and to form tacky, relatively poor quality coatings.

It is also preferred that the monomer component should contain a crosslinking component and that an external crosslinker should be employed. These measures result in a coating which maintains its integrity well below $T_m$, but which disintegrates easily when the seed expands, and which does not, therefore, interfere with germination and growth. Other measures which can be employed for the same purpose are the use of a monomer component which includes (a) at least 0.5% of at least one amphoteric monomer, and/or (b) a carboxyl-containing monomer component.

Although the foregoing description is directed principally to coating seeds for controlling the dormancy of the seed, the invention is useful for other organisms, and other purposes, e.g. to protect organisms from fungi and insects. Such other organisms include bacteria, embryos, eggs, sprouts, bugs, rhizobium, seedlings, and potato cuttings. Seeds which can be coated include vegetable seeds and grain seeds. For example, seeds for canola, maize, cotton, soybean, sugar beets, beans, tomato, potato, tobacco, corn, rice, wheat, sunflower, the brassica family, the solanaceae family, sorghum, barley, lentils, melons, cucumbers, cabbage, brussels sprouts, beans, and peas.

The composition applied to the organism can contain one or more additives, typically in amount 0.01 to 10%, preferably 0.05 to 5%, based on the composition. Suitable additives include colorants, fillers, soil pH adjusters, nutrients, seed protectors. phytotoxicity inhibitors, herbicides, growth regulators, soil improvers, fungicides, insecticides, growth stimulants, plant hormones, fertilizers, bird repellents, stimulants to accelerate growth, and innoculants. Such additives can alternatively or additionally be applied to the seed separately.

The invention is illustrated in the accompanying drawings, in which.

EXAMPLES

The invention is illustrated by the following examples, some of which are comparative examples.

Examples 1-16

Examples 1-16 illustrate the preparation of aqueous polymer dispersions. Examples 1, 5, 6, 9 and 10 are less preferred, in that the crystalline polymer does not-have a single, sharply defined melting temperature.

The following abbreviations are used in Examples 1-16 (and in the later Examples): C6A, hexyl acrylate (amorphous hydrophobic monomer); C12A, dodecyl acrylate, C14A, tetradecyl acrylate, C16A, hexadecyl acrylate, and C18A, octadecyl acrylate (all crystalline hydrophobic monomers); C6DA, 1,6-hexanediol diacrylate, and CD14A, 1,14-tetradecanediol diacrylate (both crosslinking monomers); AA, acrylic acid, and MA, methacrylic acid (both hydrophilic monomers); C12SH, dodecyl mercaptan (chain transfer agent); SP, sodium persulfate (initiator); PP, potassium persulfate (initiator); SBC, sodium bicarbonate (buffer); EAC, ethyl acetate (cosolvent); IPA, isopropanol (cosolvent).

The following are surfactants: SDS, sodium dodecyl sulfate; 15-S-7, 15-S-9 and 15-S-40 are $C_{11}$-$C_{15}$ secondary alcohol ethoxylates which are available from Union Carbide under the trade names Tergitol 15-S-7, 15-S-9 and 15-S-40, respectively; P1059, an amine salt of dodecyl benzene sulfonic acid which is available from Witco under the trade name Witconate P1059; EMC, sodium dioctyl sulfosuccinate which is available from Witco under the trade name EMCOL DOSS; SLS-R which is a 30% by weight lauryl sulfate solution in water available from Lonza, Inc under the trade name Carsonol SLS-R; and A-102 which is a disodium ethoxylated alcohol half ester of sulfosuccinic acid available from Cytec under the trade name AEROSOL A-102.

The amounts of each ingredient used in the Examples are shown in Tables 1-3.

Examples 1-8 illustrate how addition of cosolvent and high surfactant concentrations reduce the heterogeneity of emulsion polymerization reaction products prepared by using at least two different monomer components. Examples 1-4 show the effect of the addition of cosolvent in the presence of high surfactant concentrations on the heterogeneity of the polymerization reaction products. Examples 5-8 show the effect of the addition of cosolvent in the presence of low surfactant concentrations on the heterogeneity.

Examples 1-4

Figure 1:
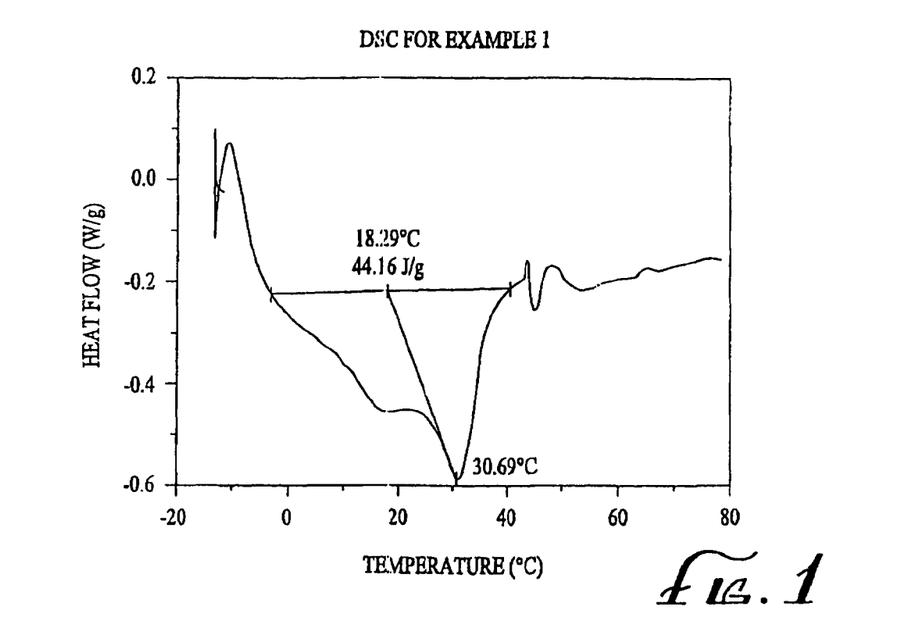
FIGS. 1-6 are DSC curves for polymers prepared in the Examples, as further described below.
Figure 2:
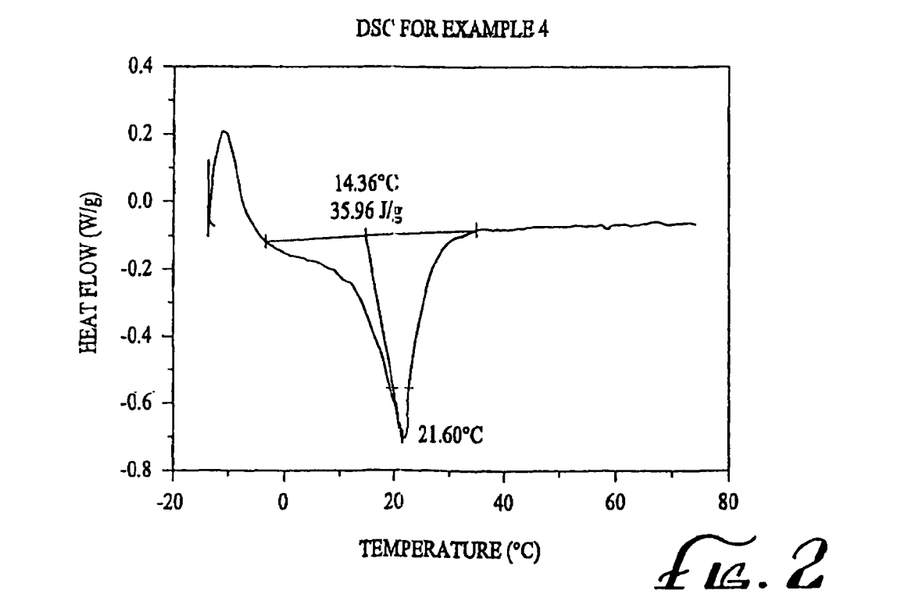

Polymers consisting of four monomer components (C16A, C6A, CD14A and MA) were prepared in the presence of a constant amount of surfactant (3.2%) and variable amounts of cosolvent as shown in Table 1. The emulsion polymerization components were mixed and degassed for 30 minutes. The polymerization reaction proceeded for 4 hours at 70° C. under nitrogen. The polymer prepared in comparative Example 1 in the absence of cosolvent exhibited a broad profile with two peaks on a DSC thermograph as shown in FIG. 1. The polymer prepared in Example 2 in the presence of 5% by weight ethanol shows a much sharper DSC peak and a lower $T_m$. The polymer prepared in Example 3 in the presence of 5% by weight ethyl acetate similarly exhibits a sharp peak. Addition of higher concentrations of ethyl acetate above 5% only has a slight effect on the sharpness of the DSC peak and the $T_m$ of the polymer product as shown in FIG. 2.

Examples 5-8

Figure 3:
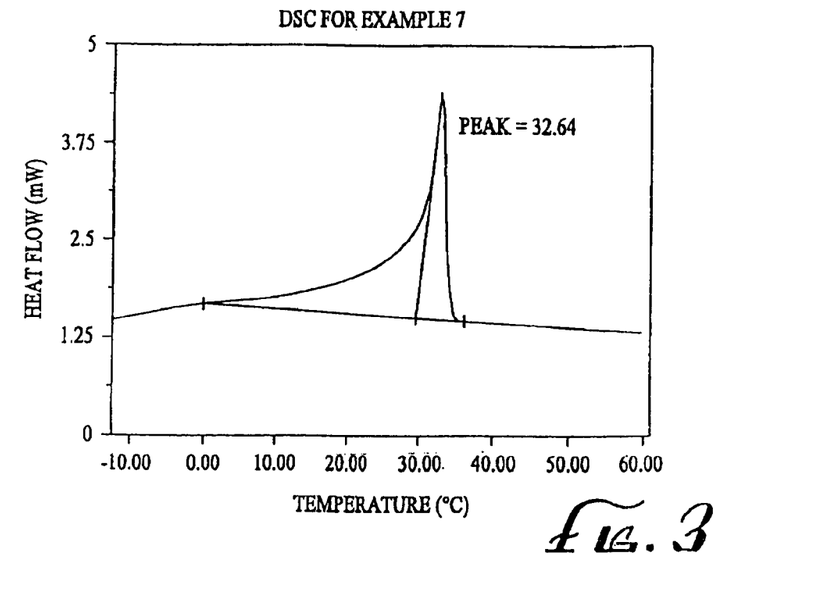

Polymers consisting of three monomer components (C16A, C6A, and MA) were prepared in the presence of a constant, but lower, amount of surfactant (1.6%) and variable amounts of cosolvent as shown in Table 1. The emulsion polymerization components were mixed and degassed for 30 minutes. The polymerization reaction proceeded for 4 hours at 70° C. under nitrogen. The polymer prepared in comparative Example 5 in the absence of cosolvent exhibits multiple DSC peaks. The polymer prepared in comparative Example 6 in the presence of 5% by weight ethyl acetate shows a single DSC peak and a lower $T_m$. The polymer prepared in Example 7 in the presence of 10% by weight ethyl acetate exhibits a sharp peak (FIG. 3). Addition of higher concentrations of ethyl acetate above 5% only has a slight effect on the sharpness of the DSC peak and the $T_m$ of the polymer product.

TABLE 1

| | Ex. 1 | Ex. 2 | Ex. 3 | Ex. 4 | Ex. 5 | Ex. 6 | Ex. 7 | Ex. 8 |
|---|---|---|---|---|---|---|---|---|
| $H_2O$ | 200 g | 190 g | 190 g | 180 g | 200 g | 190 g | 180 g | 160 g |
| C16A | 70 g | 70 g | 70 g | 70 g | 70 g | 70 g | 70 g | 70 g |
| C6A | 25 g | 25 g | 25 g | 25 g | 25 g | 25 g | 25 g | 25 g |
| MA | 5 g | 5 g | 5 g | 5 g | 5 g | 5 g | 5 g | 5 g |
| C14DA | 2 g | 1.5 g | 1.5 g | 1.5 g | — | — | — | — |
| 15-S-9 | 5 g | 5 g | 5 g | 5 g | 2.5 g | 2.5 g | 2.5 g | 2.5 g |
| P1059 | 5 g | 5 g | 5 g | 5 g | 2.5 g | 2.5 g | 2.5 g | 2.5 g |
| PP | 0.4 g | 0.4 | 0.4 g | 0.4 g | 0.4 g | 0.4 g | 0.4 g | 0.4 g |
| EAc | — | — | 10 g | 20 g | — | 10 g | 20 g | 40 g |
| Ethanol | — | 10 g | — | — | — | — | — | — |
| DSC | broad peak | sharp peak | sharp peak | sharp peak | multiple peaks | broad peak | sharp peak | sharp peak |
| $T_m$ (° C.) | 30.7 | 22.5 | 21.9 | 21.6 | 34.8 | 33.0 | 32.6 | 22.4 |

Examples 9-12

Figure 4:
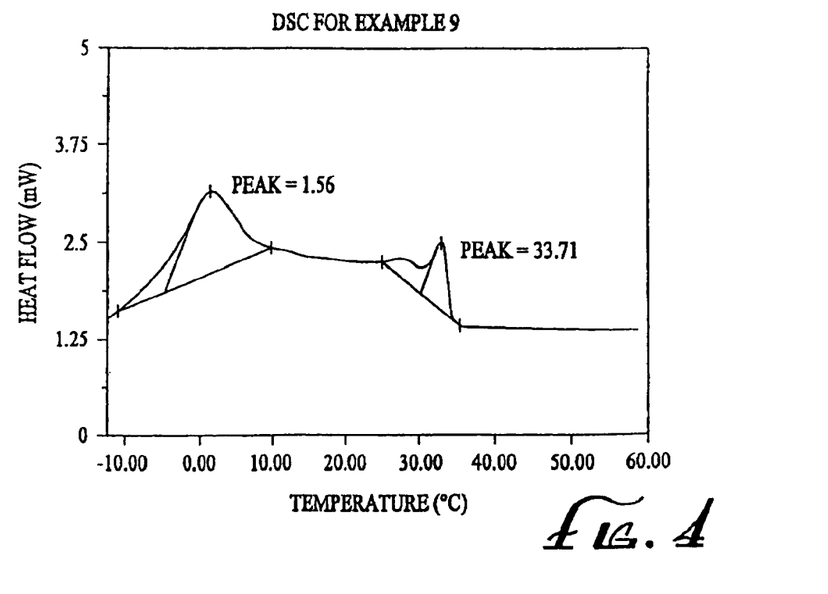
Figure 5:
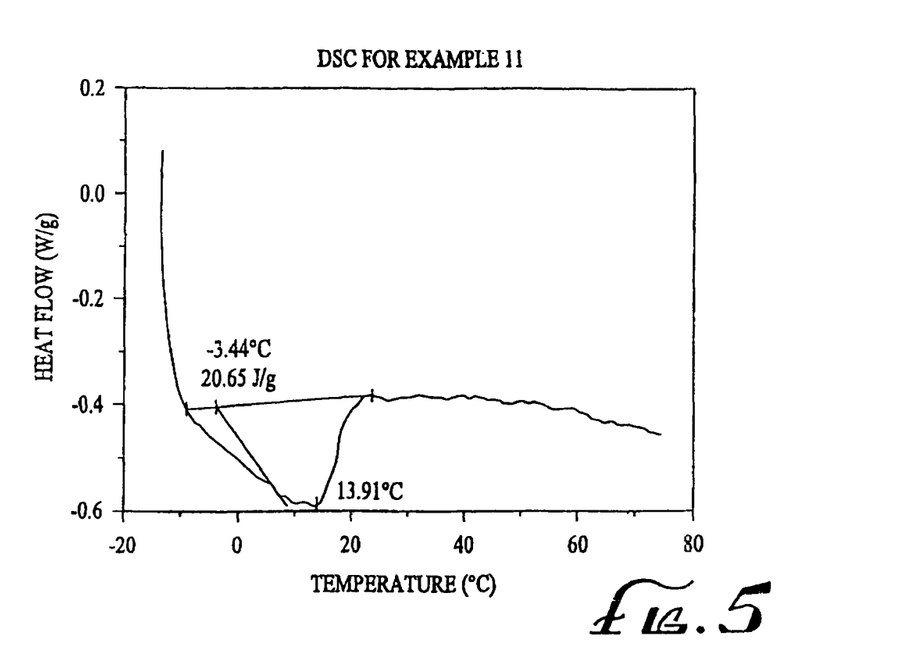
Figure 6:
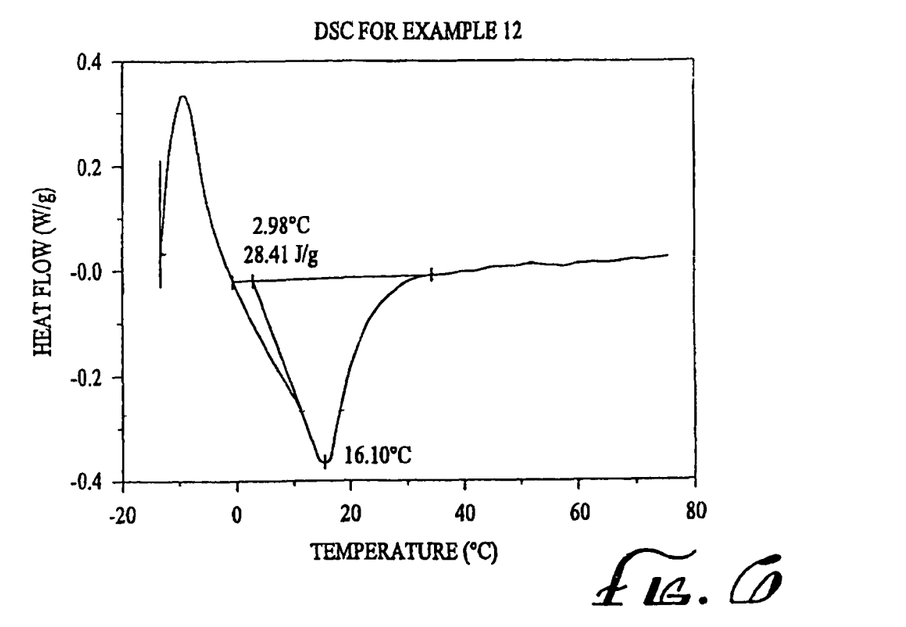
Figure 7:
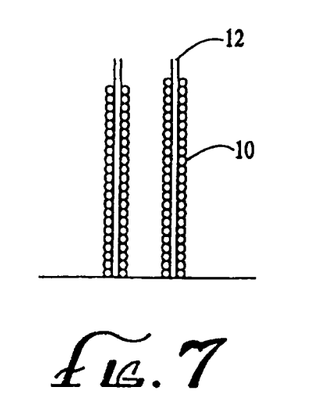
FIGS. 7 and 8 are schematic illustrations of a particulate coating 10, made up of coalesced but still identifiable particles 14, on a substrate 12, which is a fiber or a seed, respectively.
Figure 8:
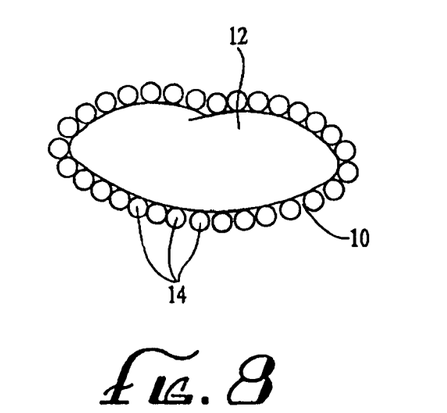

Polymers consisting of two SCC monomer components (C16A and C12A) and MA were prepared. Both C16A and C12A-based polymers are side chain crystalline polymers and can be detected by DSC whereas C6A polymers are amorphous and not detectable. The polymers were prepared in the presence of varying concentrations of surfactants and cosolvents as shown in Table 2. The emulsion polymerization components were mixed and degassed for 30 minutes. The polymerization reaction proceeded for 4 hours at 70° C. under nitrogen. The polymer prepared in comparative Example 9 in the presence of a low surfactant concentration 11.2%) in the absence of cosolvent exhibited two distinct peaks with $T_m$'s at 1.6° C. and 33.7° C. as shown in FIG. 4. The polymer prepared in comparative Example 10 in the presence of the same amount of surfactant and 5% by weight ethyl acetate shows a broad peak with three peaks with the predominant polymer species having a $T_m$ of 2.7° C. The polymer of Example 11 was prepared in the presence of higher concentrations of surfactant (2.4%). Increasing the surfactant concentration produces a polymer product with a sharp $T_m$ at 13.9° C. as shown in FIG. 5. Example 12 shows the use of different monomer components (C14A and C12A) in a reaction mixture similar to that of Example 11. Once again only one peak is observed as shown in FIG. 6.

TABLE 2

| | Ex. 9 | Ex. 10 | Ex. 11 | Ex. 12 |
|---|---|---|---|---|
| $H_2O$ | 200 g | 190 g | 400 g | 400 g |
| C16A | 35 g | 35 g | 70 g | — |
| C14A | — | — | — | 95 g |
| C12A | 60 g | 60 g | 120 g | 95 g |
| MA | 5 g | 5 g | 10 g | 10 g |
| 15-S-9 | 2 g | 2 g | 8 g | 8 g |
| DOSS | 2 g | 2 g | 8 g | 8 g |
| PP | 2 g | 0.4 g | 1.6 g | 1.5 g |
| EAc | — | 10 g | — | — |
| C12SH | — | — | — | 0.1 g |
| DSC | two peaks | broad peak | sharp peak | sharp peak |
| $T_m$ (° C.) | 2, 33.7 | 2.7 | 13.9 | 16.1 |

Examples 13-15

These examples show the large scale preparation of copolymers using the method described in this invention. Reaction components are shown in Table 3.

In Example 13 the emulsion polymerization components were mixed and degassed for 30 minutes. The polymerization reaction proceeded for 4 hours at 70° C. under nitrogen. The polymer was polymerized in the presence of a total surfactant concentration of 2.9% in the presence of 20% cosolvent. The polymer product exhibited a peak with a $T_m$ of 11.3° C.

In Example 14 the emulsion polymerization components were mixed and degassed for 30 minutes. Part of the polymerization reaction mixture (25%) was metered into a 1 liter resin kettle for 10 minutes at a rate of 12 ml/minute. The mixture was polymerized for 15 minutes at 80° C. The rest of the monomer solution was metered over 75 minutes and the polymerization reaction proceeded for 2 more hours under nitrogen. The polymer product exhibited a peak with a $T_m$ of 9° C.

In Example 15 all the polymerization components, except for the initiator, were mixed and degassed. Once the polymerization components were heated to 60° C., degassed initiator was added to the reaction mixture. The reaction proceeded for two hours while maintaining the internal temperature of the mixture at 70° C. After two hours more initiator was added to the reaction mixture to drive polymerization to completion. The reaction proceeded for a total of 5 hours. The reaction was cooled overnight. After cooling the product was neutralized to pH 7 with ammonium hydroxide and filtered with a 63 micron sieve. The polymer exhibited a single sharp peak at 9.2° C.

TABLE 3

|  | Ex. 13 | Ex. 14 | Ex. 15 |
|---|---|---|---|
| $H_2O$ | 800 g | 320 g | 4308 g |
| C14A | 405 g | 160 g | 2080 g |
| C6A | 70 g | 30 g | 390 g |
| C6DA | — | 1.4 g | 18.2 g |
| MA | 25 g | 5 g | 130 g |
| AA | — | 10 g | — |
| A-102 | 20 g | 8 g | 104 g |
| SLS | 10 g | 4 g | 52 g |
| 15-S-7 | 10 g | 4 g | 52 g |
| 15-S-40 | 2.5 g | 4 g | 13 g |
| PP | 2 g | 0.8 g | 15.6 g |
| SBC | 2 g | 0.8 g | 10.4 |
| IPA | 200 g | 80 g | 1040 g |
| DSC | sharp peak | sharp peak | sharp peak |
| $T_m$ (° C.) | 11.2 | 9.1 | 9.2 |

Example 16

A polymer was prepared with 2-acrylamido-2-methylpropane sulfonic acid (AMPS, available from Lubrizol) as follows. C16A 131.5 g), AMPS (6 g of a 50% aq. solution), water (80 g), isopropanol (20 g), Aerosol A-102 (2 g), Carsonol SLS-R (1 g) were mixed together and purged with $N_2$ for 20 min. The bottle was then capped and heated to 80° C., and 0.4 g of potassium persulfate was added. The reaction was carried out at 80° C. for 3 h. A bluish tan emulsion was formed, cooled overnight and neutralized with ammonium hydroxide.

Examples 17-24

Examples 17-24 illustrate the preparation and use of aqueous polymer dispersions for coating fibers. The molecular weights (which are given as $M_n$ values, i.e. number average molecular weights, or $M_w$ values, i.e. weight average molecular weights) were measured by the standard GPC technique in tetrahydrofuran, against polystyrene standards. The following additional abbreviations are used in these and later Examples. C4A, butyl acrylate (amorphous monomer); ESH, mercaptoethanol (chain transfer agent); AIBN, azobisisobutyronitrile (initiator); ESP, t-amylperoxy 2-ethyl hexanoate which is available from WITCO under the trade name Esperox 570 (initiator); TERG, a $C_{11}$-$C_{15}$ secondary alcohol ethoxylate which is available from Union Carbide under the trade name Tergitol 15-S-9 (surfactant).

Example 17

A mixture of C18A (1865 g), MA (150 g)) and C12SH (1 g) was added over a period of 20 minutes to a reaction vessel which was purged with nitrogen, stirred, and maintained at 100° C. Over the same period, ESP (10 g) was added separately. After 5 hours, the temperature was raised to 120° C., and heating continued for a total reaction time of 23 hours. The resulting white polymer had an $M_w$ of 198,000, $M_n$ of 26,000, $T_o$ of 43° C. and $T_p$ of 45° C.

Example 18

A sample of the polymer produced in Example 17 was finely ground and was added to a mixture of water (90 ml), TERG (1.25 g) and P-1059 (1.25 g) which was maintained at 80° C. in a stirred reaction vessel. After 2 hours of mixing, a stable emulsion had been produced.

Example 19

A mixture of C18A (95 g), MA (5 g) and C12SH (0.05 g) was added to a mixture of water (200 ml), TERG (5 g) and EMC (5 g) which was maintained at 80° C. in a stirred reaction vessel. After degassing with nitrogen for 30 minutes, PP (0.4 g) was added. Heating was maintained for 4 hours, and after the reaction mixture had cooled slowly to room temperature, it was neutralized with 10% aqueous ammonium hydroxide. The resulting milky white polymer had a $T_o$ of 43° C., $T_p$ of 47° C., and a $M_w$ above 1,500,000.

Example 20

A mixture of C16A (400 g), C12A (90 g), AA (10 g) and C12SH (105 g) was added over a period of 10 minutes to a reaction vessel which was purged with nitrogen, stirred, and maintained at 110° C. Over the same period, ESP (5 g) was added separately. Heating was continued for 4 hours. The resulting polymer had an $M_w$ of 2300, $M_n$ of 1500, $T_o$ of 21° C. and $T_p$ of 28° C.

Example 21

A mixture of toluene (200 ml), C18A (89 g), C16A (11 g), ESH (3.6 g) and AIBN (1 g) was heated under nitrogen at 60° C. for 16 hours and then at 80° C. for 2 hours. Isocyanatoethyl methacrylate (8 g) and dibutyl tin dilaurate (1 drop) were then added, and heating continued at 60° C. for 4 hours. The resulting polymer was precipitated by the addition of ethanol and was a white polymer having an $M_w$ of 5300, $M_n$ of 4080, $T_o$ of 39° C. and $T_p$ of 45° C.

A part of the resulting polymer (20 g), C4A (30 g), AIBN (0.5 g), ethyl acetate (50 ml) and heptane (50 ml) were heated under nitrogen at 60° C. for 16 hours. The resulting polymer was precipitated by the addition of ethanol and was a white thermoplastic elastomer having an $M_w$ of 516,000, $M_n$ of 34,000, $T_o$ of 39° C. and $T_p$ of 44° C.

Example 22

The procedure of Example 19 was followed except that one portion (Portion A) of the cooled reaction mixture was not neutralized and another portion (Portion B) was treated with enough sodium hydroxide to neutralize 50% of the carboxyl groups. Samples of the resulting latex were tested as follows. 300 mg samples of the latex (containing 100 mg of the polymer) were placed on glass slides, and dried at 50° C. for 1 hour. The coated slides were then placed in baths containing a 0.5% solution of Palmolive Plus dishwashing fluid in water, and maintained at 25° C. (i.e. below the $T_o$ of the polymer), 53° C. (i.e. at about the $T_p$ of the polymer) and 75° C. (i.e. well above the $T_p$ of the polymer). The baths were stirred gently and the slides were observed.

The Portion A film, at 25° C., separates from the slide after 30 minutes, without swelling or blistering; when the film, after it has separated, is lifted out of the bath on the slide and dried, it remains intact and transparent. The Portion A films, at 53° C. and 75° C., swell and blister, and separate from the slide after 25 minutes. When the films, after they have been separated, are lifted out of the baths on the slides, and dried, they show some disintegration and are opaque.

The Portion B film, at 25° C., blisters and separates from the slide after 30 minutes; after removal and drying, it remains intact and transparent. The Portion B films, at 53° C. and 75° C., blister and become opaque and separate from the slides after 3 minutes; after removal and drying, they disintegrate completely.

Example 23

The procedure of Examples 18 and 19 were followed to generate a water based emulsion of SCC polymer. The milky white formulation was applied to the hair of a doll through a pump spray bottle. The hair was then heated with a hair dryer, evaporating the water and melting the SCC polymer. While the polymer was in the molten state, the doll's hair was shaped in a desired configuration.

When the doll's hair needed to be set in another configuration, the hair was first reheated to melt the composition retained in the hair. The hair was then reshaped in the new configuration. This process was repeated several times, and each time the doll's hair retained the new desired configuration.

Example 24 (Prospective Example)

The procedure of Examples 18 or 19 is followed to generate a water based emulsion of SCC polymer. Fabric is dip coated in the milky white formulation and allowed to dry. The dried fabric is placed in the desired configuration and heated and pressed with an iron to melt the SCC polymer. The fabric is cooled in the desired configuration.

Examples 25-52

Examples 25-52 show the preparation and use of aqueous polymer dispersions for coating seeds.

The following additional abbreviations are used in these Examples TTT, 1,3,5-triallyl triazine trione (crosslinker); BDE, 1,4-butanediol divinyl ether (crosslinker); TETA, triethylene tetramine (external crosslinker); AH, 10% aqueous ammonium hydroxide available from Baxter; CC, calcium carbonate under the trade name Albaglos, 0.6 microns, available from Specialty Minerals; Zinplex 15 is available from Rohm and Haas (external crosslinker); DEAPA, N,N-Diethyl aminopropylamine is available from Aldrich (external crosslinker); Colloid 211 is a water soluble polyacrylate polymer obtained from Rhone-Poulenc that acts as a dispersant for the calcium carbonate; Defoamer 2010 is available from Dow Corning and is a low surface energy silicone polymer, and Seedmate seed colorant is a product of Loveland Industries Inc. NP, n-propanol (cosolvent).

The following is a surfactant: Lodyne S-106A, a fluorosurfactant available from Ciba-Geigy.

Examples 25-32 (Preparation of Polymer Latex)

A polymer latex for Example 25 was prepared by mixing together C16A (68 g), C6A (27 g), MA (5 g), C4DA (1 g), water (160 g), IPA (40 g), A-102 (2 g), 15-S-7 (2 g), 15-S-40 (0.5 g), and SBC (0.4 g) in a bottle. The bottle was purged with $N_2$ for 30 min. The bottle was then capped and heated to 70° C., and then PP (0.4 g) was added. The reaction was carried out at 70° C. for 4 h. The reaction exothermed rapidly and a blue latex was formed. The latex was cooled and neutralized with aqueous ammonia.

The lattices of Examples 26, 27, and 28 were prepared in the same way described for Example 1 with the same ingredients and amounts as in 25, except that TTT and BDE were substituted for C4DA in Examples 26 and 27, respectively. Example 28 was prepared in the absence of an internal crosslinker. In Example 29 an internally crosslinked polymer was prepared, where the crosslinking component was 1,4 butanediol diacrylate. The monomers were mixed together: C16A (68 g), C6A (27 g), MA (5 g), 1,4-butanediol diacrylate 11 g). An aqueous phase was prepared with water (160 g), isopropanol (40 g), Aerosol A-102 (4 g), Carsonol SLS-R (2 g), Tergitol 15-S-7 (2 g), Tergitol 15-S-40 (0.5 g), $NaHCO_3$ (0.4 g), and potassium persulfate (0.4 g). The reagents were mixed together and purged with $N_2$ for 30 minutes in a bottle. The bottle was then capped and heated to 70° C., and 0.4 g of potassium persulfate was added. The reaction was carried out at 70° C. for 4 hours. The reaction exothermed rapidly and a blue latex was formed. The latex was cooled and neutralized with aqueous ammonia.

For Example 30 a polymer was prepared with 2-acrylamido-2-methylpropane sulfonic acid (AMPS). C16A (31.5 g), AMPS 16 g of a 50% aq. solution), water (80 g), isopropanol (20 g), Aerosol A-102 (2 g), Carsonol SLS-R (1 g) were mixed together in a bottle and purged with $N_2$ for 20 min. The bottle was then capped and heated to 80° C., and 0.4 g of potassium persulfate was added. The reaction was carried out at 80° C. for 3 h. A bluish tan emulsion was formed, cooled overnight and neutralized with ammonium hydroxide.

For Example 31 a polymer was prepared in a glass lined Pflauder reactor by mixing C16A (6555 g), C6A (2470 g), MA (475 g), C6DA (66.5 g), SLS (190 g), A-102 (380 g), 15-S-7 (190 g), 15-S-40 (47.5 g), water (15,000 g) and IPA (3800 g). The mixture was sparged with nitrogen for an hour. The contents of the reactor were raised to 65 C, and an initiator solution of 38 g potassium persulfate in 380 g water as added. The reactor was maintained at 70 C for 2 hours. A chaser solution of 19 g of potassium persulfate in 380 g water was added and the reactor contents maintained at 70 C for an additional three hours, and cooled to room temperature. The latex was neutralized with AH and filtered through a 63 micron wire mesh filter.

For Example 32, a polymer was prepared in a glass lined Pflauder reactor by mixing C14A (2158 g), C6A (312 g), AA (130 g), C6DA (18.2 g), SLS (52.2 g), A-102 (105.5 g 15-S-7 (54.7 g), 15-S-40 (13 g), water (4,061 g) and IPA (1045 g). The mixture was sparged with nitrogen for 30 minutes. The contents of the reactor were raised to 65 C, and an initiator solution of 10.4 g potassium persulfate in 104 g water as added. The reactor was maintained at 70 C for 2 hours. A chaser solution of 5.2 g of potassium persulfate in 104 g water was added and the reactor contents maintained at 70 C. for an additional three hours, and cooled to room temperature. The latex was neutralized with AH and filtered through a 63 micron wire mesh filter.

Example 33

Preparation of Seed Coating Formulations

Seed coating formulations were prepared that contained:
Type I. Polymer latex containing no internal or external crosslinker (using the latex of Example 28);
Type II. Polymer latex with internal crosslinks (using the latex of Example 25);

Type II. Polymer latex prepared with an external crosslinker (using the latex of Example 28 in the presence of $Zn^{2+}$); and Type IV. Polymer latex with internal and external crosslinks (using the latex of Example 25 in the presence of TETA).

The following procedure was followed to prepare formulations of Type I and II:

A wet grind was prepared consisting of Colloid 211 (1 g), water (20 g), AH (10 g), polymer latex (100 g), and CC (120 g). The wet grind was prepared in a Cowels mixer at 3000 rpm for 30 min (shear rate 126 $sec^{-1}$). The let down was prepared by mixing (VIRTIS Shear mixing at 2000 rpm for 10 min) and consisted of wet grind (125 g), polymer latex (550 g), water (1200 g), and seed colorant (5 g). AH (10 g) was added to the formulation preparations. The let down was used directly to coat the seeds.

For Type III formulations, external crosslinker was added to the let down prior to coating. For example, Zinplex 15 (2.3 g) was added to the type I formulation during the let down (970 g) to form a coating solution. Type I formulations were prepared as follows:

CC (40 g) and water (100 g) were sheared in a VIRTIS at 2000 rpm, and Colloid 211 (0.5 g) mixed with 3 ml water was slowly added and sheared for 2 min. The latex (400 g equivalent to 120 g polymer) was made basic with 10% AH, 4-5 ml and was slowly added followed by the Zinplex and DEAPA (both diluted with 2-3 ml of water) and sheared for about 5 min. Water (500 g) and red dye (3 ml) were added. The coating solution was then filtered through a 63 micron mesh filter. Towards the end of the filtration 2 drops of defoamer were added.

For Type IV formulations, external crosslinker was added to the let-down during its preparation. For example, TTM (2.4 g) was added to the type 11 formulation let down (940 g) or Zinplex (8.6 g) was diluted with 20 g water and added to the type 11 formulation let down (1895 g). Type IV formulations were prepared as follows:

A wet grind was prepared form Colloid 211 (2 g), water (20 g), aqueous AH (20 g), latex 1250 g) and CC (360 g). The grind was mixed by blending in a Cowels mixer at 3000 rpm for 30 min. A concentrate preparation was made from wet grind (650 g), latex (2150 g), Zinplex 15 (18.4 g), and Seedmate Colorant (25 g). The coating solution was prepared by diluting the concentrate (540 g) with water (880 g).

All of these formulations have a $T_m$ of about 19-21° C.

Examples 34-46 (Seed Testing)

Seed Coating Procedure

Seeds were coated with the formulations of Example 33 using seed coating equipment for water based coatings manufactured by Diamond Coating Equipment (Tucson, Ariz.). The seed coating equipment consisted of a perforated pan fitted with baffles, and capable of handling about 20 lbs of seed/batch. The seeds were coated with a fine spray of the formulation from a spray nozzle located in the coating pan. To assist in drying of the seeds the coater was equipped with a hot air inlet and an air exhaust.

An exemplary coating procedure involving soybeans utilized Soybeans (6 kg), which were loaded into the seed coating equipment. The coating formulation was pumped to the spray nozzle using a peristaltic pump. The pan was rotated at a rate of 12-13 rpm to keep the seeds thoroughly mixed. The coating was started by turning the spray nozzle on pneumatically, and pumping at a rate of 30 ml/min. The pan temperature was maintained at 30° C. and the coating was carried out for 17 min. The spray nozzle was shut off, the pan rotation stopped, and the coated seeds were removed.

Seed Testing

Seeds were tested for water uptake and germination/plant emergence as a function of temperature under controlled conditions. The testing methods used are similar to those prescribed by the Association of Seed Analysts (AOSA) testing methods, and Rules of Testing Seeds (Association of Official Seed Analysts. Journal of Seed Technology, Vol 12, No: 3, 1988). The performance of the coated soybean seeds were measured by the water uptake of the seeds at two temperatures at 10 and 25° C. at 48 h, and the germination of the seeds at 25° C. for 7 days, and at 10° C. for 7 days followed by 7 days at 25° C. Table 2 gives the water uptake of representative coatings along with the water uptake of the uncoated seed (Example 34) used as a control.

Paper Towel Germination Test

Germination paper sheets [Anchor #38 and #76 seed germination paper (254×381 mm)] were allowed to equilibrate for about 30 min with approximately two times their dry weight of water.

Two moistened sheets were placed on the benchtop, and 10 g of seeds were placed along the length of the paper, about a third of the length from the top. Another wet sheet of paper was placed on top. A hem about 25 mm wide at the bottom was folded and the sheets rolled, and set vertically. Four to five such paper dolls were secured loosely with a pair of rubber bands and were placed vertically in a plastic bag and placed in incubators maintained at 10° C. and 25° C., respectively. After the specified amount of time (48 hours), the seeds were removed and weighed.

TABLE 2

| Example | Type | Polymer Latex | Coating Type | % Water Uptake at 10° C. | % Water Uptake at 25° C. |
| --- | --- | --- | --- | --- | --- |
| 34 | Control | No coating | No coating | 102 | 120 |
| 35 | II | C16A/C6A/AA/C14DA (68/27/5/1) | Internal X-linker | 11 | 80 |
| 36 | IV | C16A/C6A/AA/C14DA (68/27/5/1) | Int, and 0.5% Zn External | 13 | 92 |
| 37 | IV | C16A/C6A/AA/C14DA (68/27/5/1) | Int, and 2% TETA Ext | 20 | 99 |
| 38 | IV | C16A/C6A/AA/C14DA (68/27/5/1.5) | Int, 1% Zn Ext | 18 | 82 |
| 39 | IV | C16A/C6A/AA/C14DA (68/27/5/1.5) | Int, 1.5% Zn Ext | 30 | 92 |
| 40 | IV | C16A/C6A/MA/C14DA (68/27/5/1) | Int, 0.5% Zn Ext | 25 | 84 |

TABLE 2-continued

| Example | Type | Polymer Latex | Coating Type | % Water Uptake at 10° C. | % Water Uptake at 25° C. |
|---|---|---|---|---|---|
| 41 | II | C16A/C6A/MA/C14DA (68/27/5/1) | Int, no Ext | 15 | 68 |
| 42 | IV | C16A/C6A/AA/C14DA (68/27/3/1) | Int, 0.5% Zn Ext | 27 | 93 |
| 43 | III | C16A/C6A/AA (68/27/7.5) | No Int., 0.5% Zn Ext | 36 | 97 |
| 44 | II | C16A/C6A/AA/C4DA (68/27/5/1) | Int, No Ext | 20 | 96 |
| 45 | I | C16A/C6A/MA/68/27/7.5 | No Int, No Ext | 36 | 48 |
| 46 | III | C16A/C6A/MA/68/27/7.5 | No Int, 0.5% Zn Ext | 36 | 40 |

As illustrated in the Table 2 the presence of an internal crosslinker (types 11 and IV) decreased the amount of water uptake at low temperatures (10° C.) and increased the water uptake at higher temperatures (25° C.) because the seed coating fell apart more easily once the seeds started expanding. The presence of an external crosslinker improved the mechanical stability of the seed coating. Thus a combination of external and internal crosslinkers can be employed to select the water permeabilities of water coatings at various temperatures.

Example 47

A wet grind consisting of Colloid 211 (0.4 g), ammonia (0.2 g, 50/50 v/v), water (190 g) and CaCO₃ (330 g) was blended in a Cowels mixer at 3000 rpm for 30 min. The wet grind (172 g) was mixed with the polymer latex of Example 7 (C16A/C6A/MA/C6DA, 70/25/5/0.5) (705 g) ($T_m$ of 20 to 21° C.) in a VIRTIS mixer. Zinplex 15 (5.4 g diluted with 20 g water) was added slowly into the formulation followed by Lodyne S-106A (2.5 g diluted with 20 g water). Seed colorant (8 g), and water (540 g) were added to complete the formulation. The coating solution was filtered through a 60 micron wire mesh filter. Hybrid Corn (4 kg) was loaded into the seed coater, and the coating was carried out at a flow rate of 60 mL/min for a period of 11 min. The internal temperature of the pan was kept at ° 40° C.

Example 48

A wet grind was prepared by mixing in a Cowels mixer Colloid 211 (2 g), ammonium hydroxide (40 g of 10% aq. solution), the polymer latex C16A/C6A/MA/C6DA (70/25/5/0.5)) (250 g) ($T_m$ of 20 to 21° C.), and CaCO₃ (360 g) for 30 min at 3000 rpm. The concentrate was prepared from the wet grind by mixing the wet grind with the polymer latex (2150 g), and 20 g of 10% aq. ammonia. The coating solution was prepared by combining under light shear the concentrate (550 g), water (850 g), Zinplex 15 (3.6 g with 20 g water), and the seed colorant (10 g). Three kg of seeds were coated at a flow rate of 40 mL/min for 30 min. The pan temperature was maintained at 30° C.

Example 49

The formulation of Example 48 was used for coating wheat. The coating was carried out at 40 mL/min for a period of 20 min, with a pan temperature of 35° C.

Example 50

The polymer latex of Example 15 (C14A/C6A/MA/C6DA (80/15/5/0.7)) with a lower $T_m$ (12° C.) was used in the coating of sugarbeets. All other components of the formulation were identical to those described for Example 46. Sugarbeets (4 kg) were coated at a spray rate of 30 mL/min, and a pan temperature of 30° C. were coated for 40 min.

Example 51

A wet grind was prepared by blending Colloid 211 (2 g), ammonia (40 g, 10% aq. solution), latex (250 g) (C16A/C6A/AA/C14DA (70/25/8/1)), and CaCO₃ (360 g). A concentrate was prepared by mixing the wet grind with the polymer latex (2150 g) in a VIRTIS mixer, followed by 18.4 g. The cottonseeds (4 kg) were coated at a flow rate of 30 mL/min for 45 min with the pan temperature not exceeding 30° C.

Coatings on other seed varieties, including lentils, chickpeas and sweet corn, were prepared using similar formulations as described above.

Example 52

Two hybrid corn varieties from Sucrosco Seeds (Manilla, Iowa) were field tested. They were planted in Casey, Iowa. Prior to planting some of the seeds were left uncoated, other were coated with (C16A/C6A/MA/C6DA (70/25/5/0.5), 1% Zinplex) (Example 52A) or (C16A/C6A/MA/C6DA (70/25/5/0.5), 0.5% Zinplex) (Example 52B). Seed were planted at different times (23 Mar., 3 Apr. and 17 Apr., 1996) and stand counts were performed 3 weeks after planting. The results are shown in Table 3 and are the average of four different experiments.

TABLE 3

| Planting Date | Hybrid Corn Variety | Uncoated (stand count) | Example 52A Coating (stand count) | Example 52B Coating (stand count) |
|---|---|---|---|---|
| 23 March | A | 1.8 | 19 | 51 |
| 23 March | B | 23 | 44 | 69 |
| 3 April | A | 74 | 91 | 102 |
| 3 April | B | 110 | 111 | 114 |
| 17 April | A | 106 | 115 | 104 |
| 17 April | B | 110 | 119 | 121 |

As can be seen from Table 3, coating the seeds with the polymer latex coatings protect the seeds when the seeds are planted early in the planting season when there is a possibility for the seeds to suffer chilling injury. When seeds are planted later in the planting season, i.e., when it is unlikely for the soil temperature to go below 0° C., the seed coating does not have an adverse effect on corn germination because the seed coating is readily released if the temperature remains above the $T_m$ of the seed coating polymer and the seed starts expanding.

The invention claimed is:

1. A coating composition which comprises water, a surfactant, and, dispersed in the water solid particles having an average particle size of less than 0.5 micron and comprising a crystalline polymer which
   (1) has a melting point $T_m$ and an onset-of-melting temperature, $T_o$, such that $T_m$-$T_o$ is less than 20° C.,
   (2) is derived from a monomer component comprising
      (a) a hydrophobic monomer component comprising
         (i) a first hydrophobic monomer which is such that a homopolymer thereof is a side chain crystalline (SCC) polymer having a melting point $T_c$, and
         (ii) a second hydrophobic monomer which is such that a homopolymer thereof is amorphous and has a glass transition point $T_g$ which is less than $T_c$, and is from −50 to 120° C., and
      (b) a hydrophilic monomer component comprising a hydrophilic monomer,
         one or both of the hydrophobic monomer component and the hydrophilic monomer component containing at least one cross-linking monomer having at least two polymerizable groups.

2. A composition according to claim 1 wherein $T_m$ is from 40 to 60° C., and $T_m$-$T_o$ is less than 15° C.

3. A composition according to claim 1 which contains an additive selected from the group consisting of sequestering agents, hair-conditioning agents, anti-dandruff agents, reducing agents, bleaching agents, perfumes, pearlescent aids, preservatives, thickeners, coloring agents, and pH adjusting agents.

4. A composition according to claim 1 wherein (1) the hydrophobic monomer component contains 5 to 40% by weight, based on the weight of the hydrophobic monomer component, of the second hydrophobic monomer, (2) the monomer component contains 2 to 10% by weight, based on the weight of the monomer component, of the hydrophilic monomer component, and (3) the ratio by weight of the hydrophobic monomer component to the hydrophilic monomer component is 10:1 to 50:1.

5. A composition according to claim 1 wherein the first hydrophobic monomer comprises an n-alkyl acrylate wherein the n-alkyl group contains 12 to 50 carbon atoms, and the second hydrophobic monomer comprises a linear or branched chain alkyl, hydroxyalkyl or alkoxyalkyl acrylate, methacrylate, acrylamide, or methacrylamide or a vinyl ester.

6. A composition according to claim 1 wherein the surfactant comprises an anionic surfactant having an HLB number of 20 to 40 and a non-ionic surfactant having an HLB number of 5 to 35.

7. A composition which has a pH of 3 to 9, and which comprises water, a surfactant, and, dispersed in the water, 2 to 50% by weight, based on the weight of the composition, of solid particles having an average particle size of less 0.5 micron, and comprising a crystalline polymer which
   (1) has a melting point $T_m$ which is from 40 to 60° C. and an onset-of-melting temperature, $T_o$, such that $T_m$-$T_o$ is less than 15° C., and
   (2) is derived from a monomer component comprising
      (a) a hydrophobic monomer component comprising
         (i) a first hydrophobic monomer which is such that a homopolymer thereof is a side chain crystalline (SCC) polymer having a melting point $T_c$, and
         (ii) 5 to 40% by weight, based on the weight of the hydrophobic monomer component, of a second hydrophobic monomer which is such that a homopolymer thereof is amorphous and has a glass transition point $T_g$ which is less than $T_c$, and is from −50 to 120° C., and
      (b) a hydrophilic monomer component comprising a hydrophilic monomer,
         one or both of the hydrophobic monomer component and the hydrophilic monomer component containing at least one cross-linking monomer.

8. A composition according to claim 7 wherein the monomer component contains 2 to 10% by weight, based on the weight of the monomer component, of the hydrophilic monomer component, and the ratio by weight of the hydrophobic monomer component to the hydrophilic monomer component is 10:1 to 50:1.

9. A composition according to claim 7 wherein the first hydrophobic monomer comprises an n-alkyl acrylate wherein the n-alkyl group contains 12 to 50 carbon atoms, and the second hydrophobic monomer comprises a linear or branched chain alkyl, hydroxyalkyl or alkoxyalkyl acrylate, methacrylate, acrylamide, or methacrylamide or a vinyl ester.

10. A composition according to claim 7 wherein the coating composition contains an additive selected from the group consisting of sequestering agents, hair-conditioning agents, anti-dandruff agents, reducing agents, bleaching agents, perfumes, pearlescent aids, preservatives, thickeners, coloring agents, and pH adjusting agents.

11. A composition according to claim 1 wherein the amount of the cross-linking monomer is such that the crystalline polymer has a gel content of at least 50%.

12. A composition according to claim 1 wherein the amount of the cross-linking monomer is such that the crystalline polymer has a gel content of at least 60%.

13. A composition according to claim 1 wherein the amount of the cross-linking monomer is such that the polymer has a cross-linked density of at least 0.05.

14. A composition according to claim 1 wherein the amount of the cross-linking monomer is such that the polymer has a cross-linked density of at least 0.1.

15. Composition according to claim 1 wherein the first hydrophobic monomer is octadecyl acrylate, the second hydrophobic monomer is 2-ethylhexyl acrylate, the hydrophilic monomer is methacrylic acid, and the cross-linking monomer is hexanediol diacrylate.

16. A composition according to claim 7 wherein the amount of the cross-linking monomer is such that the crystalline polymer has a gel content of at least 50%.

17. A composition according to claim 7 wherein the amount of the cross-linking monomer is such that the crystalline polymer has a gel content of at least 60%.

18. A composition according to claim 7 wherein the amount of the cross-linking monomer is such that the polymer has a cross-linked density of at least 0.05.

19. A composition according to claim 7 wherein the amount of the cross-linking monomer is such that the polymer has a cross-linked density of at least 0.1.

* * * * *